United States Patent
Srinivas et al.

(10) Patent No.: US 7,375,224 B2
(45) Date of Patent: May 20, 2008

(54) ADENINE MODIFIED SILICA-BASED CATALYST, A PROCESS FOR THE PREPARATION AND USE THERE FOR THE PRODUCTION OF CYCLIC CARBONATES

(75) Inventors: Darbha Srinivas, Maharashtra (IN); Rajendra Srivastava, Maharashtra (IN); Paul Ratnasamy, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 123 days.

(21) Appl. No.: 11/438,388

(22) Filed: May 23, 2006

(65) Prior Publication Data

US 2007/0276146 A1  Nov. 29, 2007

(51) Int. Cl.
*C07F 19/00* (2006.01)
*C07D 473/00* (2006.01)
*C07D 317/08* (2006.01)

(52) U.S. Cl. ............... 544/225; 544/277; 549/229; 423/593.1

(58) Field of Classification Search .......... 423/593.1; 549/229; 544/225, 277
See application file for complete search history.

(56) References Cited

OTHER PUBLICATIONS

Lu et al., Journal of Molecular Catalysis A: Chemical, vol. 186, pp. 33-42 (2002).*
Srivastava et al., Journal fo Catalysis, vol. 233, pp. 1-15 (available online May 23, 2005).*
Alvaro et al., Journal of Catalysis, vol. 228, pp. 254-258 (2004).*
Park et al., Energy Convers. Mgmt., vol. 38, Suppl., pp. S449-S454 (1997).*

* cited by examiner

*Primary Examiner*—Porfirio Nazario-Gonzalez
(74) *Attorney, Agent, or Firm*—Oblon, Spivak, McClelland, Maier & Neustadt, P.C.

(57) ABSTRACT

The present invention provides an adenine modified solid, ordered, mesoporous, bifunctional, organo-inorganic silica-based catalyst, its method of preparation and also a process for the production of cyclic carbonates of the formula hereinbelow

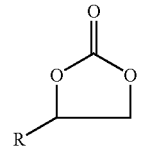

wherein R=H, $CH_2Cl$, $CH_3$, $C_4H_9$, $C_6H_{11}$, $C_6H_5$.

20 Claims, No Drawings

ADENINE MODIFIED SILICA-BASED CATALYST, A PROCESS FOR THE PREPARATION AND USE THERE FOR THE PRODUCTION OF CYCLIC CARBONATES

FIELD OF THE INVENTION

The present invention relates to adenine modified silica based catalyst, a process for the preparation thereof and its use in the production of cyclic carbonates. More particularly it relates to the said solid, ordered, mesoporous, bifunctional, organo-inorganic silica-based catalyst and a process for the preparation thereof.

The present invention also provides the use of the above said adenine modified silica based catalyst in the preparation of cyclic carbonates of formula (1)

FORMULA (1)

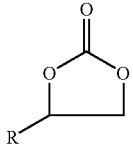

wherein R=H, $CH_2Cl$, $CH_3$, $C_4H_9$, $C_6H_{11}$ or $C_6H_5$.

BACKGROUND OF THE INVENTION

Cyclic carbonates are important raw materials for engineering plastics like polycarbonates. They are also known for their application as polar aprotic solvents, electrolytes in secondary batteries, octane booster, and, in general, intermediates in organic synthesis Plastics of aromatic polycarbonates are widely used in electric and electronic industry, building industry, optical data storage media, automotive industry, package industry, headlamp diffuser lense and bottles for water and milk. Polycarbonates of aliphatic type are used as plasticizers, stabilizers for vinyl chloride polymers, co-monomers in polyurethane synthesis, lubricants, elastomers (functionalized PC with pendent vinyl group) and biodegradable and biomedical materials for drug delivery. Aromatic polycarbonates, for example, bisphenol-A-carbonates, are commercially manufactured by condensation of 4-hydroxydiphenylbutane and phosgene ($COCl_2$) in the presence of substituted amines and alkali (Encyclopedia of Chemical Processing and Design, Vol 40, Ed. by J. J. McKetta and W. A. Cunningham, Marcel Dekker Inc., New York, 1992, p. 136 and Ulmann's encyclopedia of Industrial Chemistry, Vol. A 21, Ed. by B. Elvers, S. Hawkins and G. Schulz, $5^{th}$ ed. VCH Verlagsgesellschaft, mbH, Germany 1992, p. 207). This method of preparation employing phosgene is highly toxic and hazardous. Preparation of polycarbonates from cyclic carbonates is an alternative attractive route.

Cyclic carbonates can be synthesized through a benign route by insertion of $CO_2$ into the oxirane ring of epoxides. This is an efficient route for the utilization of $CO_2$, a "greenhouse gas", in chemicals synthesis, as an alternative to phosgene synthetic route. This reaction is catalyzed by a variety of metal catalysts from simple alkali salts and quaternary ammonium and phosphonium salts to classical organometallic complexes to different extents. Porphyrin (F. Kijima et al., J. Am. Chem. Soc. Vol. 108 (year 1986) page 391; T. Aida et al, Macromolecules Vol. 15 (year 1982) page 682 and vol. 19 (year 1986) page 8), phthalocyanine (Ji et al., Appl. Catal. A: General Vol. 203 (year 2000) page 329) and Schiff base (J. Am. Chem. Soc. Vol. 123 (year 2001) page 11498) complexes are some of those homogeneous catalysts reported to catalyze this cycloaddition reaction. Unfortunately, the metal complex catalysts that were found useful were toxic, water and air-sensitive causing handling problems and in addition required high temperature and pressure for good conversion and selectivity. In some cases high concentration of the catalyst ($\geq 1$ mol %) is required. Moreover, the processes involving these homogenous metal catalysts require additional expenses for catalyst separation and product purification.

A large number of patents have been granted towards preparing cyclic carbonate utilizing $CO_2$ and a variety of catalyst systems. For example, U.S. Pat. No. 4,824,969 (Exxon Research & Engineering Co.) reports a process for cyclic carbonate esters from olefins in a single reaction mixture using osmium compound, copper containing co-catalyst I (e.g., $CuBr_2$), co-catalyst II (e.g., pyridine) and water. U.S. Pat. No. 6,407,264 teaches a process involving the reaction of alkylene oxide with carbon dioxide in the presence of a catalyst system comprising of a metal halide and pyridine or pyridine derivative. U.S. Pat. Nos. 6,399,536, 5,391,767 and 6,288,202 and UK Pat Appl. GB 2352449 A1, PCT Int. Appl. WO 2000008088 A1, Ger. Offen. DE 19737547 A1 and Eur. Pat. Appl. EP 864361 A2 are all related to this process. U.S. Pat. No. 6,469,193 reports the preparation of aliphatic carbonates from aliphatic alcohols, alkyl halides and carbon dioxide in the presence of cesium carbonate and tetrabutyl ammonium iodide.

There are a few reports on the use of solid catalysts like silica supported guanidine (Barbarini et al Tetrahedron Lett. Vol. 44 (year 2003) page 2931) and MCM-supported phthalocyanine (Lu et al., J. Mol. Catal. A: Chemical Vol. 186 (Year 2002) page 33) for this reaction, however larger amounts catalyst and long reaction times (>15 h) are needed for high yield of cyclic carbonate. The Mg/Al oxide-based catalyst system reported earlier [K. Yamaguchi J. Am. Chem. Soc. Vol. 121 (Year 1999) page 4526], required a high catalyst loading of 1.8 g per g of substrate and, in addition, a substantial amount of solvent (85% v/v DMF) and longer reaction times (24 h).

Commercial production of cyclic carbonates by this non-phosgene route using quaternary ammonium salt-based catalysts has been announced recently by BASF (Filtration Industry Analyst 1999 (Issue No. 27, June 1999) page 2) and Chimei-Asahi Corporation (Taiwan) (S. Fukuoka et. al., Green Chem. Vol. 5 (year 2003) page 497). However, with these commercial catalysts, the reaction had to be carried out at high temperatures/pressures (30-80 bar) for high carbamate yields.

Srivastava et al (Catal. Lett. Vol. 89 (Year 2003) Page 81; Catal. Lett. Vol. 91 (Year 2003) Page 133) reported the use of metal phthalocyanines encapsulated in zeolite-Y and porous titanosilicate molecular sieves. US Pat application 20040242903 A1 reports the high performance zinc-substituted polyoxometalate solid catalysts. But in these applications an additional homogeneous Lewis base co-catalyst/promoter such as N,N-dimethyl aminopyridine is essential for high cyclic carbonate yields. This additional requirement of the homogeneous co-catalyst/promoter, hence, does not make the catalyst completely heterogeneous. Although the solid catalyst could be reused, in every recycle experiment the homogeneous, co-catalyst/promoter needs to be freshly added. It is, therefore, highly desirable to have a process for cyclic carbonate wherein the homogeneous co-catalyst/promoter can be completely avoided and the reaction occurs "truly" on the heterogeneous catalyst phase.

The present invention relates to an improved process for production of cyclic carbonates from epoxides using an adenine based completely "heterogeneous", ordered, mesoporous, bifunctional, organo-inorganic, silica-based catalyst. The solid catalyst of the present invention is a modified, mesoporous, ordered silica with a Lewis acid metal ion (preferably tetrahedral $Ti^{4+}$ ions by grafting) as well as with an organic base (preferably adenine or amine by anchoring). The catalyst is more efficient exhibiting synergism when both these constituents are present together on the mesoporous silica surface. The catalyst could be separated easily by centrifugation or by simple filtration and reused in several recycling experiments. No additional co-catalysts/promoters (unlike in the prior art catalysts) are required. Most importantly, the catalyst is highly efficient and only a small amount is needed to carryout the reaction. The process is atom-efficient and the reaction conditions like temperature and pressure are only moderate. Co-existence of dispersed, tetrahedrally coordinated Ti sites and heterogenized adenine/amine molecules and their synergism are the unique features of the catalyst of the present invention that makes this system more efficient for the cycloaddition reaction by activating the epoxide and $CO_2$ molecules, simultaneously.

The bifunctional nature of the catalyst system with these particular active sites combination facilitates the availability of more amounts of activated $CO_2$ and epoxides for the cycloaddition reaction to occur.

OBJECTIVES OF THE INVENTION

The main objective of the present invention to provide adenine modified silica based catalyst.

Another object of the present invention is to provide a process for the preparation of adenine modified silica based catalyst.

Yet another object is to provide an efficient process for the preparation of cyclic carbonates in high yields by using adenine modified silica based catalyst.

Still another object is to provide a process for the production of cyclic carbonates wherein use of toxic phosgene is eliminated.

In the investigations leading to the present invention, it was found that the ordered, mesoporous, bifunctional, silica-based catalyst is highly efficient and could be easily separated from the products and reused. Both the Ti ion (weak Lewis acid sites) and adenine moieties (the basic sites) are necessary for maximum catalytic activity and selectivity. The prior art catalysts need additional expenses for catalyst separation. An easily separable catalyst system e.g., the catalyst of the present invention is beneficial and leads to a green catalytic process. Hence, the solid catalysts of the present invention are not only efficient but avoid the tedious process of catalyst recovery characteristic of the prior art processes and eliminate the presence of toxic elements like metal ions and nitrogen-containing molecules in the products and effluents. If these impurities are allowed to be present in the product they are expected to modify the physical and chemical properties of the products. The present catalyst system is efficient even when the reactions are carried out in absence of any solvent. The present invention does not involve the toxic phosgene reactants and hence, unlike the conventional process it is safer.

SUMMARY OF THE INVENTION

Accordingly the present invention provides an adenine modified solid, ordered, mesoporous, bifunctional, organo-inorganic silica-based catalyst having molar composition

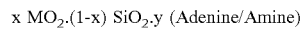

x $MO_2$.(1-x) $SiO_2$.y (Adenine/Amine)

wherein, x ranges between 0.008 to 0.03 moles, y varies between 0.054 to 0.12 and M=Ti.

In an embodiment of the present invention the catalyst has the following characteristics:

| | |
|---|---|
| XRD Peaks (degrees) | 0.88, 1.5, 1.7 |
| Space group | p6 mm, 2D hexagonal |
| Unit cell parameter | 11.7 nm |
| Interplanar spacing $d_{100}$ (from XRD) | 10 nm |
| Surface area | 627 $m^2/g$ |
| Total pore volume | 1.04 $cm^3/g$ |
| Mesopore volume | 0.96 $cm^3/g$ |
| Micropore volume | 0.08 $cm^3/g$ |
| Pore diameter | 6.7 nm |
| $SiO_2/TiO_2$ (molar ratio) | 40 |
| $SiO_2$/Adenine (molar ratio) | 0.0183 |
| $CO_2$ adsorption (from temperature programmed desorption in the range 25-250° C.) | 5.3 mmol per g of catalyst |
| $NH_3$ adsorption (from temperature programmed desorption in the range 50-350° C.) | 1 mmol per g of catalyst |
| FT-IR band for covalently anchored Adenine | 3300 $cm^{-1}$ |
| Diffuse reflectance UV-visible band for covalently anchored adenine | 266 nm (asymmetric) |
| Diffuse reflectance UV-visible band for dispersed tetrahedral $Ti^{4+}$ ions and | 211 nm |
| The catalyst is recyclable for reuse. | |

The present invention further provides a process for the preparation of the adenine modified solid, ordered, mesoporous, bifunctional, organo-inorganic silica-based catalyst having molar composition

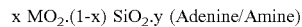

x $MO_2$.(1-x) $SiO_2$.y (Adenine/Amine)

wherein, x ranges between 0.008 to 0.03 moles, y varies between 0.054 to 0.12 and M=Ti, the said process comprising the steps of:
a) dispersing triblock copolymer poly-ethylene glycol-block-polypropylene glycol-block-polyethylene glycol in water, adding dil. hydrochloric acid to the above said dispersion and heating it to a temperature of about 40° C. to obtain the homogenous polymer solution,
b) adding tetraethyl orthrosilicate to the above said polymer solution under stirring to obtain the gel and allowing the stirring to continue for a period of 16 to 24 hrs.,
c) autoclaving the above said gel, at a temperature of 95 to 105° C., for a period of 40 to 48 hrs., followed by filtration to separate out the resultant solid, washing the resultant product with water and calcining it at a temperature ranging between 500 to 550° C., for a period of 6 to 8 hrs. to obtain the SBA-15 material,
d) preparing a mixture of glycerol, tetra propyl ammonium hydroxide (TPAOH) and the titanium source,
e) adding SBA-15 material obtained in step (c) to the above said solution mixture obtained in step (d) and stirring the resultant mixture, at a temperature ranging between 80 to 140° C., for a period of 36 to 80 hrs., followed by filtration to removing the glycerol and calcining the catalyst so obtained, at a temperature ranging between 400 to 500° C., for a period of 4 to 6 hrs to obtain the Ti-SBA-15 material, f) activating the above said Ti-SBA-15, under vacuum, at a temperature of 150 to 200° C., for a period of 1 to 5 hrs., g) adding a solution of 3-chloropropyltriethoxysilane in dry toluene to the above said activated Ti-SBA-15 material and refluxing the resultant mixture, under inert atmosphere (nitrogen or argon), for a period of 6 to 12 hrs., followed by soxhlet extraction with organic solvent to obtain the propylchloride-functionalized Ti-SBA-15 material (Ti-SBA-15-pr-Cl), h) preparing a solution of adenine in DMF, under inert environment, at temperature ranging between 100 to 140° C., i) adding Ti-SBA-15-pr-Cl obtained in step (g) to the above said solution of adenine and stirring the resultant mixture, for a period of 6 to 12 hrs. to obtain the solid adenine modified catalyst, and separating the solid product by filtration, followed by its extraction in organic solvents by known methods to obtain the desired adenine modified silica-based catalyst.

In an embodiment of the present invention the concentration of poly-ethylene glycol-block-polypropylene glycol-polyethylene used is in the range of 10-15 gms in 75 ml of water (w/v)

In yet another embodiment the amount of 3-chloropropyltriethoxysilane used is in the range of 24 mmol per gram of silica SBA-15.

In yet another embodiment the organic solvent used in step (g) for soxhlet extraction is selected from dichloromethane, acetone, and acetonitrile.

In yet another embodiment the molar ratio of glycerol, tetra propyl ammonium hydroxide (TPAOH) and titanium source used is in the range of 20-40:2-8:0.1-1.0.

In yet another embodiment the organic solvent used in step (h) for product extraction is acetonitrile.

In yet another embodiment the concentration of adenine is 1 to 5 wt % of solid Ti-SBA-15.

In yet another embodiment the titanium source is titanium tertabutyl orthotitanate or titanium isopropxide.

In yet another embodiment the catalyst obtained is useful for the preparation of cyclic carbonates.

In yet another embodiment the catalyst obtained is recyclable for further use.

The present invention further provides a process for production of cyclic carbonates of formula (1)

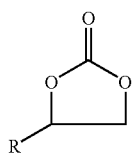

FORMULA (1)

wherein R=H, $CH_2Cl$, $CH_3$, $C_4H_9$, $C_6H_{11}$ or $C_6H_5$, using adenine modified silica based solid catalyst which comprises contacting an epoxide and carbon dioxide with adenine modified silica-based catalyst, optionally in presence of a solvent, at a temperature in the range of 80° C. to 120° C., a pressure of 2 bar to 7 bar, for a period of 2 to 8 hrs, cooling the above said reaction mixture to a temperature of 20-25° C. and removing the unreacted $CO_2$, followed by the separation of the catalyst by filtration to obtain the desired product of cyclic carbonate.

In yet another embodiment the epoxide used is selected from the group consisting of ethylene oxide, propylene oxide, chloropropylene oxide, butylene oxide, styrene oxide, cyclohexene oxide and their derivatives thereof.

In yet another embodiment the adenine modified silica-based catalyst used is having a molar composition x $MO_2$.(1-x) $SiO_2$.y (Adenine/Amine)

wherein, x ranges between 0.008 to 0.03 moles, y varies between 0.054

In yet another embodiment the cyclic carbonate obtained is selected from the group consisting of ethylene carbonate, propylene carbonate, chloropropylene carbonate, butylene carbonate, styrene carbonate and cyclohexene carbonate.

In yet another embodiment the molar ratio of epoxide to Lewis Acid ($Ti^{4+}$ in catalyst) used is in the range of 430-1120.

In yet another embodiment the molar ratio of epoxide to adenine (in catalyst) used is in the range of 80-200.

In yet another embodiment the mol % conversion of epoxide is in the range of 84-95%.

In yet another embodiment the mol % selectivity for carbonate is in the range of 89-95%.

In feature of the present invention, by using the solid orgnanic-inorganic hybrid catalyst of the present invention, homogeneous co-catalyst/promoters such as N,N dimethyl aminopyridine and related molecules which are otherwise essential in the prior art catalyst/processes are avoided and the reaction occur completely on a heterogeneous catalyst surface.

The process of the present invention is described herein below with examples, which are illustrative only and should not be construed to limit the scope of the present invention in any manner.

EXAMPLE 1

This example illustrates the preparation of the catalyst of the present invention. In the preparation of the catalyst of the present invention, first mesoporous silica SBA-15 was prepared according to following procedure. In a typical synthesis, 2 g of amphiphilic triblock copolymer, poly(ethylene glycol)-block-poly(propylene glycol)-block-poly(ethylene glycol) ($EO_{20}PO_{70}EO_{20}$; average molecular weight=5800, Aldrich Co.), was dispersed in 15 g of water and 60 g of 2 M HCl solution while stirring, followed by the addition of 4.25 g of tetraethyl orthosilicate (TEOS, Aldrich Co.) to the homogeneous solution. This gel was continuously stirred at 40° C. for 24 h, and finally crystallized in a Teflon-lined steel autoclave at 100° C. for 2 days. After crystallization, the solid product was centrifuged, filtered, washed with deionized water, and dried in air at room temperature (25° C.). The material was calcined at 550° C. for 6 h to decompose the triblock copolymer and obtain a white powder SBA-15. It was then titanated as per the following procedure. In a typical preparation, a certain amount of TBOT was hydrolyzed in 40 mL of glycerol (99 wt %, s. d. fine Chem. Ltd.) containing 7.5 mL of tetrapropylammonium hydroxide (TPAOH; 20 wt %, Aldrich Co.), to obtain a homogeneous solution. To this solution was added 2 g of SBA-15 without any pretreatment, and the mixture was heated statically at 100° C. for 72 h to induce titanation. Ti-SBA-15, thus obtained, was filtered, washed with deionized water, and the organic species were burnt off at 500° C. for 4 h. Titanated mesoporous silica referred as Ti-SBA-15 contains a final Si/Ti molar composition of 40. Organofunctionalization of titanated mesoporous silica (Ti-SBA-15) with done as follows: Ti-SBA-15 was activated under vacuum at 150° C. for about 3 h. To it, 3-chloropropyltriethoxysilane (9 mmol per 3 g of silica support; Lancaster) in 100 ml of dry toluene was added and refluxed under nitrogen for 6 h. Soxhlet extraction with dichlomethane (for 12 h) and then with acetone (for 12 h) yielded propylchloride-functionalized Ti-SBA-15 material (Ti-SBA-15-pr-Cl). This was then condensed with adenine to get adenine functionalized Ti-SBA-15 (referred as Ti-SBA-15-pr-Ade). In a typical condensation procedure, adenine (1.76 mmol, 0.238 g) was taken in 30 ml of dry DMF and stirred for 30 min under nitrogen environment at 120° C. for complete dissolution. Then, 1.5 g of Ti-SBA-15-pr-Cl was added and stirring was continued for 12 h. The solid was filtered, Soxhlet extracted with DMF (for 10 h) and then with $CH_3CN$ (for 12 h).

EXAMPLE 2

This example reports the preparation procedure of propylamine-functionalized Ti-SBA-15 (referred as Ti-SBA-15-pr-$NH_2$). In a typical synthesis, Ti-SBA-15 was initially, activated under vacuum at 150° C. for about 3 h. To it, 3-aminopropyltriethoxysilane (9 mmol per 3 g of Ti-SBA-15; Lancaster) in 100 ml of dry toluene was added and refluxed under nitrogen for 6 h. Soxhlet extraction with dichlomethane (for 12 h) and then with acetone (for 12 h) yielded propylamine-functionalized Ti-SBA-15 (refereed as Ti-SBA-15-pr-$NH_2$).

Ti-SBA-15 was activated under vacuum at 150° C. for about 3 h. To it, 3-chloropropyltriethoxysilane (9 mmol per 3 g of silica support; Lancaster) in 100 ml of dry toluene was added and refluxed under nitrogen for 6 h. Soxhlet extraction with dichlomethane (for 12 h) and then with acetone (for 12 h) yielded propylchloride-functionalized Ti-SBA-15 material (Ti-SBA-15-pr-Cl). This was then condensed with adenine to get adenine functionalized Ti-SBA-15 (referred as Ti-SBA-15-pr-Ade). In a typical condensation procedure, adenine (1.76 mmol, 0.238 g) was taken in 30 ml of dry DMF and stirred for 30 min under nitrogen environment at 120° C. for complete dissolution. Then, 1.5 g of Ti-SBA-15-pr-Cl was added and stirring was continued for 12 h. The solid was filtered, Soxhlet extracted with DMF (for 10 h) and then with $CH_3CN$ (for 12 h).

EXAMPLE 3

This example illustrates the preparation of adenine-functionalized mesoporous silica SBA-15 (hereafter referred as SBA-15-pr-Ade). Initially, SBA-15 was activated under vacuum at 150° C. for about 3 h. To it, 3-chloropropyltriethoxysilane (9 mmol per 3 g of silica SBA-15; Lancaster) in 100 ml of dry toluene was added and refluxed under nitrogen for 6 h. Soxhlet extraction with dichlomethane (for 12 h) and then with acetone (for 12 h) yielded propylchloride-functionalized SBA-15 (hereafter referred as SBA-15-pr-Cl). This was then condensed with adenine to get adenine functionalized SBA-15 (referred as SBA-15-pr-Ade). In a typical condensation procedure, adenine (1.76 mmol, 0.238 g) was taken in 30 ml of dry DMF and stirred for 30 min under nitrogen environment at 393 K for complete dissolution. Then, 1.5 g of SBA-15-pr-Cl was added and stirring was continued for 12 h. The solid was filtered, Soxhlet extracted with DMF (for 10 h) and then with $CH_3CN$ (for 12 h).

EXAMPLE 4

This example illustrates the procedure for the preparation of chloropropylene carbonate from epichlorohydrin and carbon dioxide using Ti-SBA-15 (Si/Ti molar ratio=40) catalyst. In a typical reaction 18 mmol of epichlorohydrin, 100 mg of Ti-SBA-15 were taken in a 300 ml stainless steel pressure reactor. The reactor was pressurized to 100 psig with $CO_2$ and then the temperature was raised to 120° C. Reaction was conducted for 4 hrs. The reactor was then cooled to 25° C., unreacted $CO_2$ was vented out, catalyst was separated by filtration and the products were diluted with dichloromethane and analyzed by GC (Varian 3400) and identified by GC-MS (Shimadzu QP-5000), FT-IR (Perkin Elmer 2000) and $^1H$ NMR (Bruker AC 200).

EXAMPLE 5

This example illustrates the procedure for the preparation of chloropropylene carbonate from epichlorohydrin and carbon dioxide using SBA-15-pr-Ade catalyst. In a typical reaction 18 mmol of epichlorohydrin, 100 mg of SBA-15-pr-Ade were taken in a 300 ml stainless steel pressure reactor. The reactor was pressurized to 100 psig with $CO_2$ and then the temperature was raised to 120° C. Reaction was conducted for 4 hrs. The reactor was then cooled to 25° C., unreacted $CO_2$ was vented out, catalyst was separated by filtration and the products were diluted with dichloromethane and analyzed by GC (Varian 3400) and identified by GC-MS (Shimadzu QP-5000), FT-IR (Perkin Elmer 2000) and $^1H$ NMR (Bruker AC 200).

EXAMPLE 6

This example illustrates the procedure for the preparation of chloropropylene carbonate from epichlorohydrin and carbon dioxide using Ti-SBA-15-pr-Ade (Si/Ti molar ratio=40) catalyst. In a typical reaction 18 mmol of epichlorohydrin, 100 mg of Ti-SBA-15-pr-Ade were taken in a 100 ml stainless steel pressure reactor. The reactor was pressurized to 100 psig with $CO_2$ and then the temperature was raised to 120° C. Reaction was conducted for 4 hrs. The reactor was then cooled to 25° C., unreacted $CO_2$ was vented out, catalyst was separated by filtration and the products were diluted with dichloromethane and analyzed by GC (Varian 3400) and identified by GC-MS (Shimadzu QP-5000), FT-IR (Perkin Elmer 2000) and $^1H$ NMR (Bruker AC 200).

EXAMPLE 7

This example illustrates the procedure for the preparation of propylene carbonate from propylene oxide and carbon dioxide using Ti-SBA-15-pr-Ade (Si/Ti molar ratio=40) catalyst. In a typical reaction 18 mmol of propylene oxide, 100 mg Ti-SBA-15-pr-Ade (40) were taken in a 100 ml stainless steel pressure reactor. The reactor was pressurized to 100 psig with $CO_2$ and then the temperature was raised to 120° C. Reaction was conducted for 6 hrs. The reactor was then cooled to 25° C., unreacted $CO_2$ was vented out, catalyst was separated by filtration and the products were diluted with dichloromethane and analyzed by GC (Varian 3400) and identified by GC-MS (Shimadzu QP-5000), FT-IR (Perkin Elmer 2000) and $^1H$ NMR (Bruker AC 200).

EXAMPLE 8

This example illustrates the procedure for the preparation of styrene carbonate from styrene oxide and carbon dioxide using Ti-SBA-15-pr-Ade (Si/Ti molar ratio=40) catalyst and. In a typical reaction 18 mmol of styrene oxide and 100 mg of Ti-SBA-15-pr-Ade were taken in a 100 ml stainless steel pressure reactor. The reactor was pressurized to 100 psig with $CO_2$ and then the temperature was raised to 120° C. Reaction was conducted for 8 hrs. The reactor was then cooled to 25° C., unreacted $CO_2$ was vented out, catalyst was separated by filtration and the products were diluted with dichloromethane and analyzed by GC (Varian 3400) and identified by GC-MS (Shimadzu QP-5000), FT-IR (Perkin Elmer 2000) and $^1H$ NMR (Bruker AC 200).

EXAMPLE 9

This examples illustrates the recyclability of the Ti-SBA-15-pr-Ade catalyst system in chloropropylene carbonate synthesis. In a typical procedure the used catalyst Ti-SBA-15-pr-Ade (Si/Ti molar ratio=40) in example 6 is washed first with acetonitrile and then with acetone and dried at 110° C. for 1 h. It was then used in the catalysis run and the experiments was conducted in a similar manner as reported in example 6. The catalyst was recycled in 3 experiments.

The catalytic activity data of various modified catalysts are listed in TABLE 2. Spectral characteristics of the product cyclic carbonate are as follows:

Chloropropylene carbonate—IR(cm$^{-1}$): $v_{C=O}$, 1800, $v_{C-O}$, 1133, 1080;
$^1H$ NMR (CDCl$_3$), δ(ppm): 5.03-4.94 (1H, m), 4.61-4.52 (1H, q), 4.44-4.35 (1H, q), 3.84-3.74 (2H, m).

Propylene carbonate—IR(cm$^{-1}$): $v_{C=O}$, 1793, $v_{C-O}$, 1121, 1078;
$^1H$ NMR (CDCl$_3$), δ(ppm): 4.88-4.77 (1H, m), 4.55-4.49 (1H, t), 4.01-3.96 (1H, t), 1.45 (3H, d).

Styrene carbonate—IR(cm$^{-1}$): 1812, 1163, 1062 ($v_{C=O}$);
$^1H$ NMR (CDCl$_3$), δ(ppm): 7.47-7.3 (5H, m), 5.73-5.63 (1H, t), 4.83-4.75 (1H, t), 4.37-4.29 (1H, t).

TABLE 2

Synthesis of cyclic carbonates over titanosilicate catalysts

| Example | Catalyst | Epoxide | Epoxide conversion (mol %) | Selectivity for cyclic carbonate (mol %) |
|---|---|---|---|---|
| 4 | Ti-SBA-15 | Epichlorohydrin | 20.1 | 86.3 |
| 5 | SBA-15-pr-Ade | Epichlorohydrin | 80.5 | 75.0 |
| 6 | Ti-SBA-15-pr-Ade (40) | Epicholorhydrin | 93.9 | 89.0 |
| 7 | Ti-SBA-15-pr-Ade (40) | Propylene oxide | 89.2 | 91.7 |
| 8 | Ti-SBA-15-pr-Ade (40) | Styrene oxide | 94.0 | 94.6 |
| 9 | Ti-SBA-15-pr-Ade(40) | Epichlorohydrin | 84.0 | 88.8 |
| | Recycle-I | | 80.1 | 88.9 |
| | Recycle-II | | | |

The process described above has the combined unique advantages of high epoxide conversion accompanied with high selectivity for cyclic carbonate.

The process is eco-friendly and does not involve toxic reactants like phosgene. The catalyst can be easily separated from the product mixture and reused with no significant loss in activity/selectivity.

The catalysts of the present invention are highly efficient for the preparation of cyclic carbonates from epoxides and carbon dioxide.

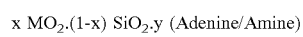

We claim:

1. An adenine modified solid, ordered, mesoporous, bifunctional, organo-inorganic silica-based catalyst having molar composition x MO$_2$.(1-x) SiO$_2$.y (Adenine/Amine)

wherein, x ranges between 0.008 to 0.03 moles, y varies between 0.054 to 0.12 and M=Ti.

2. A catalyst as claimed in claim 1 has the following characteristics:

| | |
|---|---|
| XRD Peaks (degrees) | 0.88, 1.5, 1.7 |
| Space group | p6 mm, 2D hexagonal |
| Unit cell parameter | 11.7 nm |
| Interplanar spacing d$_{100}$ (from XRD) | 10 nm |
| Surface area | 627 m$^2$/g |
| Total pore volume | 1.04 cm$^3$/g |
| Mesopore volume | 0.96 cm$^3$/g |
| Micropore volume | 0.08 cm$^3$/g |
| Pore diameter | 6.7 nm |
| SiO$_2$/TiO$_2$ (molar ratio) | 40 |
| SiO$_2$/Adenine (molar ratio) | 0.0183 |
| CO$_2$ adsorption (from temperature programmed desorption in the range 25-250° C.) | 5.3 mmol per g of catalyst |
| NH$_3$ adsoprition (from temperature programmed desorption in the range 50-350° C.) | 1 mmol per g of catalyst |
| FT-IR band for covalently anchored Adenine | 3300 cm$^{-1}$ |
| Diffuse reflectance UV-visible band for covalently anchored adenine | 266 nm (asymmetric) |
| Diffuse reflectance UV-visible band for dispersed tetrahedral Ti$^{4+}$ ions and | 211 nm |
| The catalyst is recyclable for reuse. | |

3. A process for the preparation of the adenine modified solid, ordered, mesoporous, bifunctional, organo-inorganic silica-based catalyst having molar composition x MO$_2$.(1-x) SiO$_2$.y (Adenine/Amine)

wherein, x ranges between 0.008 to 0.03 moles, y varies between 0.054 to 0.12 and M=Ti, the said process comprising the steps of:

a) dispersing triblock copolymer poly-ethylene glycol-block-polypropylene glycol-block-polyethylene glycol in water, adding dilute hydrochloric acid to the above said dispersion and heating it to a temperature of about 40° C. to obtain the homogenous polymer solution, b) adding tetraethyl orthroslilicate to the above said polymer solution under stirring to obtain the gel and allowing the stirring to continue for a period of 16 to 24 hrs., c) autoclaving the above said gel, at a temperature of 95 to 105° C., for a period of 40 to 48 hrs., followed by filtration to separate out the resultant solid, washing the resultant product with water and calcining it at a temperature ranging between 500 to 550° C., for a period of 6 to 8 hrs. to obtain the mesoporous silica (SBA-15) material, d) preparing a mixture of glycerol, tetra propyl ammonium hydroxide (TPAOH) and the titanium source, e) adding SBA-15 material obtained in step (c) to the above said solution mixture obtained in step (d) and stirring the resultant mixture, at a temperature ranging between 80 to 140° C., for a period of 36 to 80 hrs., followed by filtration to removing the glycerol and calcining the catalyst so obtained, at a temperature ranging between 400 to 500° C., for a period of 4 to 6 hrs to obtain the titanated mesoporous silica (Ti-SBA-15) material, f) activating the above said Ti-SBA-15, under vacuum, at a temperature of 150 to 200° C., for a period of 1 to 5 hrs., g) adding a solution of 3-chloropropyltriethoxysilane in dry toluene to the above said activated Ti-SBA-15 material and refluxing the resultant mixture, under inert atmosphere (nitrogen or argon), for a period of 6 to 12 hrs., followed by soxhlet extraction with organic solvent to obtain the propylchloride-functionalized Ti-SBA-15 material (Ti-SBA-15-pr-Cl), h) preparing a solution of adenine in DMF, under inert environment, at temperature ranging between 100 to 140° C., i) adding Ti-SBA-15-pr-Cl obtained in step (g) to the above said solution of adenine and stirring the resultant mixture, for a period of 6 to 12 hrs. to obtain the solid adenine modified catalyst, and separating the solid product by filtration, followed by its extraction in organic solvents by known methods to obtain the desired adenine modified silica-based catalyst.

4. A process as claimed in claim 3 wherein the concentration of poly-ethylene glycol-block-polypropylene glycol-polyethylene used is in the range of 10-15 gms in 75 ml of water (w/v).

5. A process as claimed in claim 3, wherein the amount of 3-chloropropyltriethoxysilane used is in the range of 2-4 mmol per gram of silica SBA-15.

6. A process as claimed in claim 3 wherein the organic solvent used in step (g) for soxhlet extraction is selected from dichloromethane, acetone, and acetonitrile.

7. A process as claimed in claim 3, wherein the molar ratio of glycerol, tetra propyl ammonium hydroxide (TPAOH) and titanium source used is in the range of 20-40:2-8:0.1-1.0.

8. A process as claimed in claim 3, wherein the organic solvent used in step (h) for product extraction is acetonitrile.

9. A process as claimed in claim 3 the concentration of adenine is 1 to 5 wt % of solid Ti-SBA-15.

10. A process as claimed in claim 3 the titanium source is titanium tertabutyl orthotitanate or titanium isopropxide.

11. A process as claimed in claim 3, wherein the catalyst obtained is useful for the preparation of cyclic carbonates.

12. A process as claimed in claim 3, wherein the catalyst obtained is recyclable for further use.

13. A process for production of cyclic carbonates of formula (1)

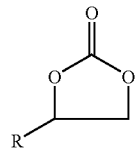

FORMULA (1)

wherein R=H, $CH_2Cl$, $CH_3$, $C_4H_9$, $C_6H_{11}$ or $C_6H_5$, using adenine modified silica based solid catalyst which comprises contacting an epoxide and carbon dioxide with adenine modified silica-based catalyst, optionally in presence of a solvent, at a temperature in the range of 80° C. to 120° C., a pressure of 2 bar to 7 bar, for a period of 2 to 8 hrs, cooling the above said reaction mixture to a temperature of 20-25° C. and removing the unreacted $CO_2$, followed by the separation of the catalyst by filtration to obtain the desired product of cyclic carbonate.

14. A process as claimed in claim 13, wherein the epoxide used is selected from the group consisting of ethylene oxide, propylene oxide, chloropropylene oxide, butylene oxide, styrene oxide, cyclohexene oxide and their derivatives thereof.

15. A process as claimed in claim 13, wherein the adenine modified silica-based catalyst used is having a molar composition x $MO_2$.(1-x) $SiO_2$.y (Adenine/Amine)

wherein, x ranges between 0.008 to 0.03 moles, y varies between 0.054 to 0.12 and M=Ti.

16. A process as claimed in claim 13, wherein the cyclic carbonate obtained is selected from the group consisting of ethylene carbonate, propylene carbonate, chloropropylene carbonate, butylene carbonate, styrene carbonate and cyclohexene carbonate.

17. A process as claimed in claim 13, wherein the molar ratio of epoxide to Lewis Acid ($Ti^{4+}$ in catalyst) used is in the range of 430-1120.

18. A process as claimed in claim 13, wherein the molar ratio of epoxide to adenine (in catalyst) used is in the range of 80-200.

19. A process as claimed in claim 13, wherein the mol % conversion of epoxide is in the range of 84-95%.

20. A process as claimed in claim 13, wherein the mol % selectivity for carbonate is in the range of 89-95%.